(12) United States Patent
Karargyris et al.

(10) Patent No.: US 11,763,931 B2
(45) Date of Patent: Sep. 19, 2023

(54) RULE OUT ACCURACY FOR DETECTING FINDINGS OF INTEREST IN IMAGES

(71) Applicant: MERATIVE US L.P., Ann Arbor, MI (US)

(72) Inventors: Alexandros Karargyris, San Jose, CA (US); Chun Lok Wong, San Jose, CA (US); Joy Wu, San Jose, CA (US); Mehdi Moradi, San Jose, CA (US)

(73) Assignee: MERATIVE US L.P., Ann Arbor, MI (US)

( * ) Notice: Subject to any disclaimer, the term of this patent is extended or adjusted under 35 U.S.C. 154(b) by 1137 days.

(21) Appl. No.: 16/377,944

(22) Filed: Apr. 8, 2019

(65) Prior Publication Data

US 2020/0321101 A1    Oct. 8, 2020

(51) Int. Cl.
*G06T 7/00* (2017.01)
*G16H 30/40* (2018.01)
(Continued)

(52) U.S. Cl.
CPC .......... *G16H 30/40* (2018.01); *G06F 18/217* (2023.01); *G06F 18/2148* (2023.01); *G06F 18/24* (2023.01); *G06F 40/169* (2020.01); *G06N 20/00* (2019.01); *G06T 7/0012* (2013.01); *G06V 10/774* (2022.01); *G06V 10/776* (2022.01); *G16H 15/00* (2018.01); *G06F 40/30* (2020.01);
(Continued)

(58) Field of Classification Search
CPC ...... G16H 30/40; G16H 15/00; G06F 40/169; G06F 40/30; G06F 40/253; G06K 9/6257; G06K 9/6262; G06K 9/6267; G06K 9/6256; G06N 20/00; G06N 3/0454; G06N 3/082; G06N 3/084; G06T 7/0012; G06T 2207/10116; G06T 2207/20081; G06V 2201/031
See application file for complete search history.

(56) References Cited

U.S. PATENT DOCUMENTS 8,391,574 B2    3/2013  Collins et al.
10,169,863 B2   1/2019  Reicher et al.
(Continued)

OTHER PUBLICATIONS

Anonymous, "Techniques to Securely Identify Abnormal Patient Records in a Post-Processed Medical Workflow", BM Confidential, Jan. 20, 2011, ip.com, 8 pages.

*Primary Examiner* — Tom Y Lu
(74) *Attorney, Agent, or Firm* — Michael Best & Friedrich LLP

(57) ABSTRACT

Methods and systems are directed to training an artificial intelligence engine. One system includes an electronic processor configured obtain a set of reports corresponding to a set of medical images, determine a label for a finding of interest, and identify one or more ambiguous reports in the set of repots. Ambiguous reports do not include a positive label or a negative label for the finding of interest. The electronic processor is also configured to generate an annotation for each of the one or more ambiguous reports in the set of reports, and train the artificial intelligence engine using a training set including the annotation for each of the one or more ambiguous reports and non-ambiguous reports in the set of reports. A result of the training is generation of a classification model for the label for the finding of interest.

20 Claims, 8 Drawing Sheets

(51) Int. Cl.
  *G06N 20/00* (2019.01)
  *G16H 15/00* (2018.01)
  *G06F 40/169* (2020.01)
  *G06F 18/24* (2023.01)
  *G06F 18/21* (2023.01)
  *G06F 18/214* (2023.01)
  *G06V 10/774* (2022.01)
  *G06V 10/776* (2022.01)
  *G06F 40/30* (2020.01)

(52) U.S. Cl.
  CPC .............. *G06T 2207/10116* (2013.01); *G06T 2207/20081* (2013.01)

(56) References Cited

U.S. PATENT DOCUMENTS

| | | | |
|---|---|---|---|
| 10,910,100 B2* | 2/2021 | Harzig | G16H 50/20 |
| 10,936,628 B2* | 3/2021 | Cao | G06F 16/51 |
| 11,049,243 B2* | 6/2021 | Odry | G06K 9/6245 |
| 2017/0046498 A1 | 2/2017 | Reicher | |
| 2017/0337329 A1 | 11/2017 | Liu et al. | |
| 2018/0060533 A1 | 3/2018 | Reicher et al. | |
| 2018/0060535 A1 | 3/2018 | Reicher et al. | |
| 2020/0334566 A1* | 10/2020 | Vianu | G06N 3/084 |

* cited by examiner

RULE OUT ACCURACY FOR DETECTING FINDINGS OF INTEREST IN IMAGES

FIELD OF DISCLOSURE

Embodiments described herein relate to image analysis. More particularly, embodiments described herein relate to systems and methods for improving rule-out accuracy relating to detection of a finding of interest in images.

SUMMARY

Chest X-rays (CXR) are one of the most commonly performed medical imaging exams as part of the initial diagnostic workup and screening processes in various clinical settings. Artificial intelligence (AI) can be trained to aid in CXR reads by ruling out certain findings. Classifiers built for such applications are often trained on large datasets that derive labels from clinical notes written for patients.

Although the quality of the positive findings described in these notes is often reliable, lack of the mention of a finding does not always rule out the presence of the finding. Lack of mention in notes can happen because radiologists comment on the patient in the context of the exam. As an example, a radiologist may focus on trauma as opposed to chronic disease when evaluating images obtained in emergency rooms. However, disease finding ambiguity can negatively affect the performance of AI algorithms. Accordingly, modeling the ambiguity during AI model training can improve performance of the AI system.

In particular, embodiments described herein provide systems and methods for training an AI engine. The system includes an electronic processor and memory storing instructions that, when executed by the electronic processor, cause the system to obtain a set of reports corresponding to a set of medical images, determine a label for a finding of interest, identify one or more ambiguous reports in the set of reports, generate an annotation for each of the one or more ambiguous reports in the set of reports, and train the AI engine using a training set including the annotation for each of the one or more reports and non-ambiguous reports in the set of reports, thereby generating a classification model for the label for the finding of interest. In some embodiments, the one or more ambiguous reports do not include a positive label (i.e., presence of a radiology finding) or a negative label (i.e., non-presence of a radiology finding) for the finding of interest.

Another embodiment provides a method for training an AI engine hosted on a server. The method includes obtaining a set of reports corresponding to a set of medical images, determining a label for a finding of interest, applying natural language processing to the set of reports, identifying one or more ambiguous reports in the set of reports, generating an annotation for each of the one or more ambiguous reports in the set of reports, and training the AI engine using a training set including the annotation for each of the one or more ambiguous reports and non-ambiguous reports in the set of reports, thereby generating a classification model for the finding of interest. In some embodiments the annotation for each of the one or more ambiguous reports is generated using an electronic processor. In some embodiments, the one or more ambiguous reports do not include a positive label or a negative label for the finding of interest.

A further embodiment provides non-transitory computer-readable medium including instructions that, when executed by an electronic processor, perform a set of functions. The set of functions includes obtaining a set or reports corresponding to a set of medical images, determining a label for a finding of interest, applying natural language processing to the set of reports, identifying one or more ambiguous reports in the set of reports, generating an annotation for each of the one or more ambiguous reports in the set of reports, and training the AI engine using a training set including the annotation for each of the one or more ambiguous reports and non-ambiguous reports in the set of reports, thereby generating a classification model for the finding of interest. In some embodiments, the one or more ambiguous reports do not include a positive label or a negative label for the finding of interest.

Other aspects of the disclosure will become apparent by consideration of the detailed description and accompanying drawings.

DETAILED DESCRIPTION

Figure 1:
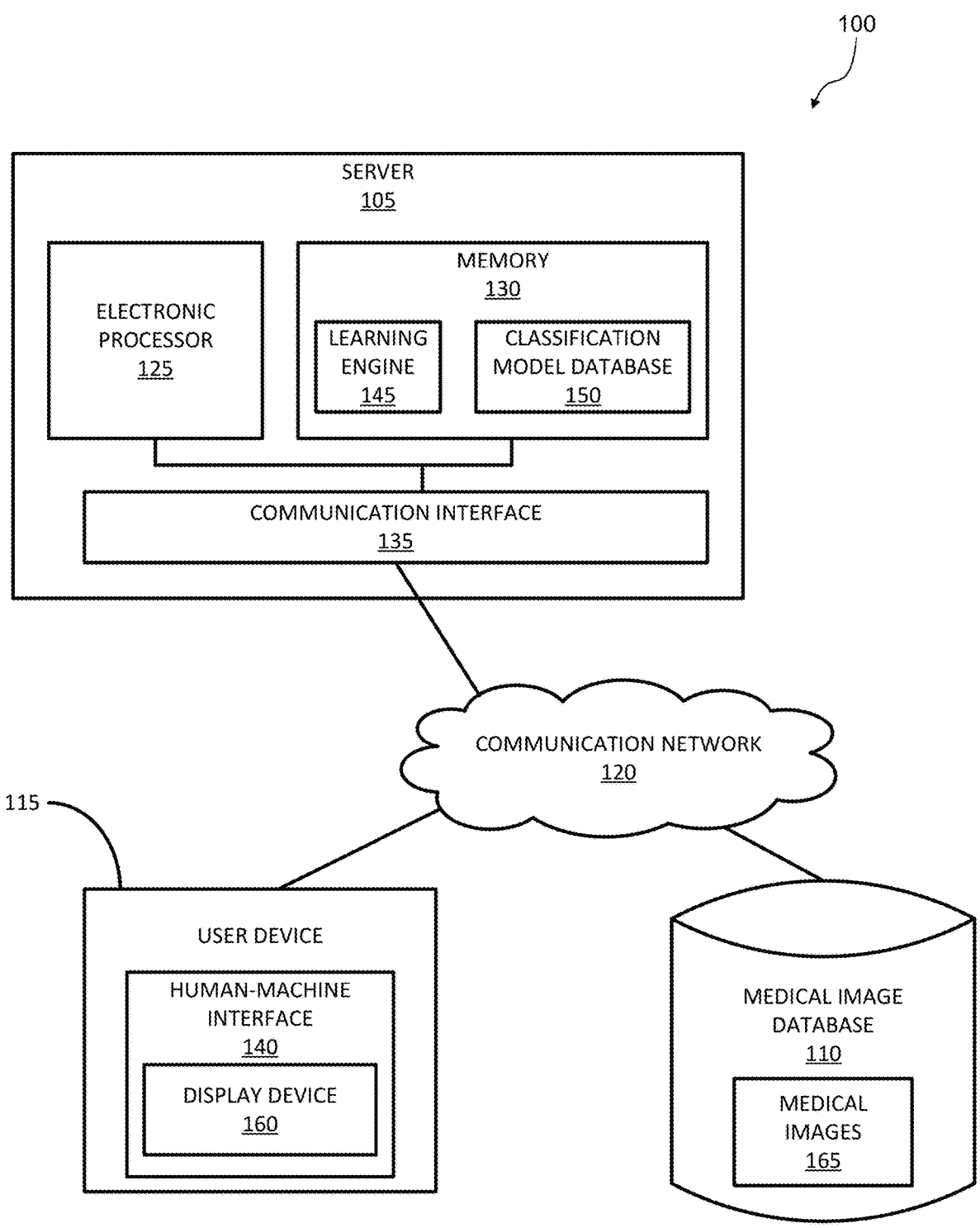
FIG. 1 illustrates an example system for training an artificial intelligence engine (AI) according to some embodiments.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used herein, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

Also, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Example systems and methods disclosed and contemplated herein relate to training and optimizing classifiers for artificial intelligence (AI) analysis engines. Although the following description focuses on disease-finding classifiers in a medical context, it will be appreciated that various systems, methods, and techniques disclosed herein are applicable to other domains, such as autonomous vehicles. For example, with the autonomous vehicle space, images may be labeled to identify a road center line, a stop sign, or other findings of interested similar to findings of interest in medical images.

As mentioned above, public datasets of classified images can be used to train AI models. However, many radiology reports, such as CXR reports, do not include complete data for training, particularly with respect to labels for a finding of interest. As used herein, a "finding of interest" is a particular objective that the image is being evaluated for. For instance, for CXRs, a finding of interest might be pneumothorax. As used herein, a "label" is an indication that the finding of interest is, or is not, present in the given image. Example labels include affirmed ("a positive label") and negated ("a negative label") labels.

Most CXR radiology reports can be categorized as indicating one of the following: (1) a finding label was affirmed/positive, (2) a finding label was negated/negative, or (3) the finding label was not mentioned in the CXR radiology report. In fact, because CXR is often used as a screening exam to rule out abnormal findings, a large number of sentences in most CXR reports may specifically mention that some findings are not present (negated). An example would be no pneumothorax, pleural effusion and consolidation. Therefore, directly predicting a negated finding output for some findings could be just as useful clinically as a positive finding prediction, because the information is still helpful in guiding the subsequent patient management.

However, there is also the no mention category for all the different finding types, which represent an even larger proportion of the whole label space than the negated/not present findings. Given the wide clinical applications of CXRs and over a hundred different types of findings of varying prevalence, there are multiple reasons why any finding might not be mentioned in the radiology report. The no mention cases might be attributed to: true negation or false negative. True negation means that the finding label is not present but also clinically not important enough to specifically negate in report. False negative means that the finding is present but the radiologist missed it, or did not think it was clinically relevant enough to mention in that particular setting (e.g. reporting an irrelevant chronic finding like shoulder arthritis in an acute trauma case). Accordingly, adjusting the training of classifiers built using natural language processed-labelled image collections to handle the no mention cases avoids discarding a large amount of CXR examples that were essentially partially labeled, which decreases the available training information and subsequently effects the accuracy of the resulting model. Accordingly, embodiments described herein are directed to optimizing training of a disease finding classifier in situations where both positive and negated labels are present, by addressing the uncertainties of the no mention cases in each label.

FIG. 1 illustrates a system 100 for training an AI engine according to some embodiments. The system 100 includes a server 105, a medical image database 110, and a user device 115. In some embodiments, the system 100 includes fewer, additional, or different components than illustrated in FIG. 1. For example, the system 100 may include multiple servers 105, medical image databases 110, user devices 115, or a combination thereof.

The server 105, the medical image database 110, and the user device 115 communicate over one or more wired or wireless communication networks 120. Portions of the communication network 120 may be implemented using a wide area network, such as the Internet, a local area network, such as a Bluetooth™ network or Wi-Fi, and combinations or derivatives thereof. Alternatively or in addition, in some embodiments, components of the system 100 communicate directly as compared to through the communication network 120. Also, in some embodiments, the components of the system 100 communicate through one or more intermediary devices not illustrated in FIG. 1.

The server 105 is a computing device, which may serve as a gateway for the medical image database 110. For example, in some embodiments, the server 105 may be a commercial picture archive and communication system (PACS) server. Alternatively, in some embodiments, the server 105 may be a server that communicates with a PACS server to access the medical image database 110.

As illustrated in FIG. 1, the server 105 includes an electronic processor 125, a memory 130, and a communication interface 135. The electronic processor 125, the memory 130, and the communication interface 135 communicate wirelessly, over one or more communication lines or buses, or a combination thereof. The server 105 may include additional components than those illustrated in FIG. 1 in various configurations. The server 105 may also perform additional functionality other than the functionality described herein. Also, the functionality described herein as being performed by the server 105 may be distributed among multiple devices, such as multiple servers included in a cloud service environment. In addition, in some embodiments, the user device 115 may be configured to perform all or a portion of the functionality described herein as being performed by the server 105.

The electronic processor 125 includes a microprocessor, an application-specific integrated circuit (ASIC), or another suitable electronic device for processing data. The memory 130 includes a non-transitory computer-readable medium, such as read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, another suitable memory device, or a combination thereof. The electronic processor 125 is configured to access and execute computer-readable instructions ("software") stored in the memory 130. The software may include firmware, one or more applications, program data, filters, rules, one or more program modules, and other executable instructions. For example, the software may include instructions and associated data for performing a set of functions, including the methods described herein.

For example, as illustrated in FIG. 1, the memory 130 may store a learning engine 145 and a classification model database 150. It should be understood that in some embodiments, the classification model database 150 may be located external to the server 105. In this embodiment, the server 105 may communicate with and access data from the classification model database 150 directly or through one or more of the communication network(s) 120. Also, in some embodiments, the classification model database 150 may be included in or part of the medical image database 110, the user device 115, or a combination thereof, which the server 105 may similarly access.

The communication interface 135 allows the server 105 to communicate with devices external to the server 105. For example, as illustrated in FIG. 1, the server 105 may communicate with the medical image database 110 through the communication interface 135. In particular, the communication interface 135 may include a port for receiving a wired connection to an external device (for example, a universal serial bus (USB) cable and the like), a transceiver for establishing a wireless connection to an external device (for example, over one or more communication networks 120, such as the Internet, local area network (LAN), a wide area network (WAN), and the like), or a combination thereof.

The server 102 may also communicate with user device 115 via the communication network 120. Broadly, a user, such as a clinician, uses user device 115 to interact with one or more of the learning engine 145, the classification model database 250, and the medical image database 110. Although not illustrated, the user device 115 may include similar components as the server 105 (an electronic processor, a memory, and a communication interface). As noted above, in some embodiments, a memory of the user device 115 may store the classification model database 150. Alternatively or in addition, the user device 115 may access the classification model database 150 (or a portion thereof) stored in the memory 130 of the server 105 (or another device external to the user device 115) via the communication network 120.

The user device 115 may also include a human-machine interface 140. The human-machine interface 140 may include one or more input devices, one or more output devices, or a combination thereof. Accordingly, in some embodiments, the human-machine interface 140 allows a user to interact with (for example, provide input to and receive output from) the user device 115. For example, the human-machine interface 140 may include a keyboard, a cursor-control device (for example, a mouse), a touch screen, a scroll ball, a mechanical button, a display device (for example, a liquid crystal display (LCD)), a printer, a speaker, a microphone, or a combination thereof. As illustrated in FIG. 1, in some embodiments, the human-machine interface 140 includes a display device 160. The display device 160 may be included in the same housing as the user device 115 or may communicate with the user device 115 over one or more wired or wireless connections. For example, in some embodiments, the display device 160 is a touchscreen included in a laptop computer or a tablet computer. In other embodiments, the display device 160 is a monitor, a television, or a projector coupled to a terminal, desktop computer, or the like via one or more cables.

The medical image database 110 stores a plurality of medical images 165. As noted above, in some embodiments, the medical image database 110 is combined with the server 105. Alternatively or in addition, the medical images 165 may be stored within a plurality of databases, such as within a cloud service. Although not illustrated in FIG. 1, the medical image database 110 may include components similar to the server 105, such as an electronic processor, a memory, a communication interface, and the like. For example, the medical image database 110 may include a communication interface configured to communicate (for example, receive data and transmit data) over the communication network 120.

In some embodiments, the medical image database 110 stores additional data associated with the medical images 165, such as a classification associated with each of the medical images 165 and/or clinician notes associated with one or more of the medical images 165 as described below in more detail. Accordingly, in some embodiments, the medical image database 110 stores the training information used to train the classification models stored in the classification model database 150. In other embodiments, this information (along with the associated image data) may be stored separate from the medical image database 110. The medical image database 110 may also store acquired or captured medical images that are not part of a training dataset.

The server 105 can be configured to use natural language processing to extract data from structured and unstructured medical documentation stored in the medical image database 110 (or other devices). Example data included in the medical documentation includes imaging reports, notes, diagnoses, findings, etc. A commercially available solution for such extraction activities includes the IBM Watson Health Patient Synopsis and Clinical Review.

The learning engine 145 applies machine learning (artificial intelligence) to mimic cognitive functions, including but not limited to learning and problem solving. Machine learning generally refers to the ability of a computer program to learn without being explicitly programmed. In some embodiments, a computer program (sometimes referred to as a learning engine) is configured to construct a model (for example, one or more algorithms) based on example inputs. Supervised learning involves presenting a computer program with example inputs and their desired (actual) outputs. The computer program is configured to learn a general rule (a model) that maps the inputs to the outputs in the training data.

Machine learning may be performed using various types of methods and mechanisms. Example methods and mechanisms include decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using some or all of these approaches, a computer program may ingest, parse, and understand data and progressively refine models for data analytics, including image analytics. Once trained, the computer system may be referred to as an intelligent system, an artificial intelligence (AI) system, a cognitive system, or the like. Accordingly, in some embodiments, the learning engine 145 includes Watson® provided by IBM Corporation. The learning engine 145 may be "trained" using various machine learning techniques. In some embodiments, the learning engine 145 may be trained using an image training dataset of chest x-rays.

In some embodiments, the learning engine 145 (when executed by the electronic processor 125) develops a classification model using one or more machine learning functions, and classification models generated by the learning engine 145 may be stored in the classification model database 150. A developed classification model can then be used to determine findings of interest for images, such as CXRs.

Figure 2:
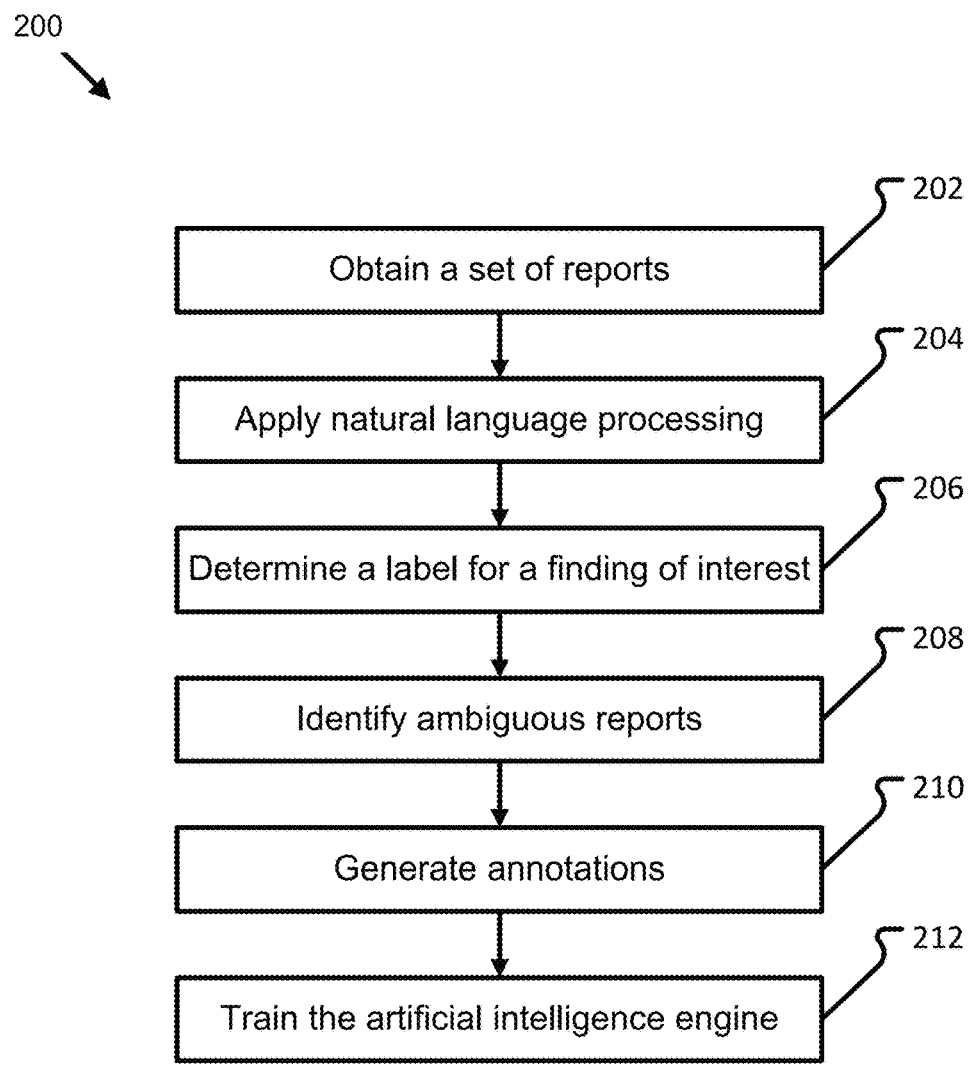
FIG. 2 is a flowchart illustrating an example method for training an AI engine performed by the system of FIG. 1.

FIG. 2 shows an example method 200 for training an artificial intelligence engine (the learning engine 145) to generate one or more models, such as a classification model. Generally, the method 200 is directed to training an artificial intelligence engine to generate one or more models for identifying one or more labels for a finding of interest in an image, such as a CXR. In some embodiments, as discussed above, the server 105 can be configured to execute one or more operations of method 200 (through execution of the electronic processor 125). However, in other embodiments, functionality included in the method 200 (or a portion thereof) may be performed by other devices, including other servers, a medical image database, a user device, or the like. It should also be understood that, in other embodiments, the method 200 includes fewer or additional steps in other orders or configurations.

As illustrated in FIG. 2, the method 200 includes obtaining a set of reports (at block 202). The set of reports correspond to a set of medical images. The reports might be handwritten (images of handwritten papers) or machine readable files, such as word processing documents and spreadsheets. The reports include notes and/or diagnosis data regarding a finding of interest in a medical image included in the corresponding set of medical images (image study). In some instances, obtaining the set of reports also includes obtaining the corresponding sets of medical images.

The server 105 may obtain the set of reports by communicating with one or more remote servers (including, for example, the medical image database 110, to request and receive report data, which can include CxR images, clinician notes, and labels. In some instances, the remote servers are operated by different entities or institutions. The set of reports might be stored in publicly available databases.

As illustrated in FIG. 2, in some embodiments, the method 200 optionally includes applying natural language processing to the set of reports (at block 204). Natural language processing includes processing and analyzing natural language data (general or free-form text data) to identify or recognize words or phrases of interest. Natural language processing can include applying context recognition natural language processing to identify findings of interest and an associated label from text entered by a radiologist into a report. In some embodiments, a report may be formatted such that labels for a finding of interest are readily available without requiring natural language processing (e.g., using mark-up languages or other types of data fields or data formatting).

The method 200 also includes determining a label for a finding of interest within an associated image (at block 206). Determining the label for the finding of interest can also include using natural language processing as received above identify one or more terms within a report indicating that a particular finding was affirmed or negated. For example, in some instances, determining the label for the finding of interest includes parsing or analyzing one or more sentences of text.

Determining a label for the finding of interest may result in identifying ambiguous reports (at block 208). Reports that do not have a positive label or a negative label for the finding of interest are termed "ambiguous reports." Usually, at least some reports in the dataset are ambiguous. In some instances, about 30%, about 40%, about 50%, or even greater percentages, of the reports in the dataset may be ambiguous for a given finding of interest. Ambiguous reports can be identified (operation 208) by those reports where operation 206 did not determine either a positive label or a negative label for the finding of interest.

As illustrated in FIG. 2, an annotation (non-ambiguous label) is generated for each ambiguous report identified in the set of reports (at block 210). In one sense, the annotation is an "educated" guess about whether the finding of interest is affirmed or negated for the particular medical image (or images) associated with the ambiguous report. Accordingly, generating an annotation may include applying either a positive label or a negative label to the finding of interest within ambiguous reports. In some embodiments, a normal distribution is used to assign labels to the ambiguous reports. However, it should be understood that other distributions can be used to assign labels, although other types of distributions can be used. A normal distribution can be based on any domain-focused data. For instance, when clinical data indicates that a typical dataset would have a given percentage of negative labels for a particular finding of interest, then generating annotations can include applying labels to the ambiguous reports to conform to that expectation. In some instances, at least 80%; at least 85%; at least 90%; or at least 95% of the annotations for the ambiguous reports are negative labels. However, it should be understood that these percentages are provided as examples and other percentages are possible.

After applying the annotations to the ambiguous reports, each report in the dataset now has a non-ambiguous label for a finding of interest. This full set of reports can be referred to as a "training set," and can be used to train an AI engine, such as the learning engine 145 (at block 212). Again, the training set includes the annotated ambiguous reports as well as the labeled (i.e., non-ambiguous) reports from the set of reports. Training the learning engine 145 using the training set may result in generation one or more classification models for the finding of interest. Accordingly, this classification model can be applied in subsequent analyses of images to automatically generate a label (positive or negative) for the particular finding of interest.

Example Implementation

An example implementation is described below, without limitation, to illustrate various aspects of the disclosed systems and methods.

I. Methods and Setup

In the example implemented, a deep neural network for producing findings for a CXR report was created, using a large number of labeled images obtained by automatic text analysis of reports accompanied by the Medical Information Mart for Intensive Care III (MIMIC-III) dataset.

A. Label Extraction

In this implementation, label extraction was performed using a top-down knowledge-driven plus a bottom up text curation process to identify a set of unique finding concepts relevant for CXRs. In this implementation, a NLP concept expansion engine was used to semantically map the different ways a finding could be described in reports to a discrete finding label set validated by radiologists. Then context recognition NLP was applied to differentiate between negated and affirmed instances for each finding mention. Where CXR reports did not mention a finding, the report was flagged as a "no mention" case. The three most frequently occurring finding labels were chosen, and their negated versions, to conduct the experiments described herein.

B. Class Weights and Loss Function

For each semantic label, the numbers of positive and negated samples can be highly unbalanced, and the class with the higher frequency can dominate the loss function and lead to suboptimal classifiers. Therefore, class weights can be used to alleviate this issue. In this implementation, the class weights were computed as:

$$w_1 = \frac{f_0}{f_1 + f_0}, w_0 = 1 - w_1 \quad (1)$$

With $w_1$ and $w_0$ being the weights for the positive and negated classes, and $f_1$ and $f_0$ being the numbers of the positive and negated samples, respectively. The loss of each semantic label can then be computed as the weighted binary cross-entropy:

$$L = w_1(-y \ln(p)) + w_0(1-y)(-\ln(1-p)) \quad (2)$$

where $y=1$ for positive samples and 0 otherwise. $p \in [0,1]$ is the sigmoid output from the network prediction. The average loss of all semantic labels is used for the backpropagation.

C. Class Weight Modifiers

With the introduction of negations in the semantic labels, the interpretation of a sample with both negatives (0, 0) for a pair (a semantic label and its negation, e.g. "consolidation" and "no consolidation") can be ambiguous. For example, Table 1 below shows the possible combinations of a negated pair.

TABLE 1

Meanings of different combinations of a negated pair (a semantic label A and its negation $A_0$)

| A | $A_0$ | Meaning |
|---|---|---|
| 1 | 1 | Contradiction |
| 1 | 0 | A exists |
| 0 | 1 | $A_0$ exists |
| 0 | 0 | Ambiguous |

For a semantic label, as the positives (1's) are explicitly mentioned by radiologists, they are certain findings. On the other hand, the negatives (0's) are not mentioned and can be ambiguous, because apart from the negative meaning of the semantic label, the 0's can also mean the finding is missed or not considered. For example, for the negated label "no consolidation," a 0 can mean there is consolidation or "no consolidation" is not considered at all. Therefore, the (1, 1) pair is contradicting and should not exist, the (1, 0) and (0, 1) pairs should follow the meanings of 1's as they are conscious annotations, and the (0, 0) pair is ambiguous.

To handle such ambiguity in training, the weight modifiers were used to modify the class weights of each sample with the (0, 0) negated pair when computing the loss function. In fact, although 0's are ambiguous in general, the level of ambiguity is different between a semantic label and its negation. For example, for findings such as "consolidation," the chance of being missed or not considered should be low because radiologists are trained to report anomalies. For the negations such as "no consolidation," the chance of being not considered is high because radiologists are usually not required to explicitly mention non-existence of all findings. Therefore, the weight modifiers for a semantic label (m) and its negation ($\bar{m}$) can be different and can be given as:

$$m = N(\mu, \sigma), \bar{m} = 1 - m \quad (3)$$

with $N(\mu, \sigma)$ being the normal or Gaussian distribution with mean $\mu$ and standard deviation $\sigma$. Besides Gaussian distribution, other types of probability distributions can be applied in the same principle The standard deviation in this implementation was fixed at a value of 0.05. The weight modifiers m and $\bar{m}$ are multiplied by $w_0$ in (1) during training. A larger m means a semantic label is trusted more than its negation, and vice versa. Accordingly, instead of a constant m, a normal distribution was used to model the un-certainties caused by ambiguity.

D. Network Architectures

To show that the proposed weight modifiers are generally applicable, experiments were performed on a custom architecture, and also on a widely used architecture DenseNet neural network architecture.

Figure 3:
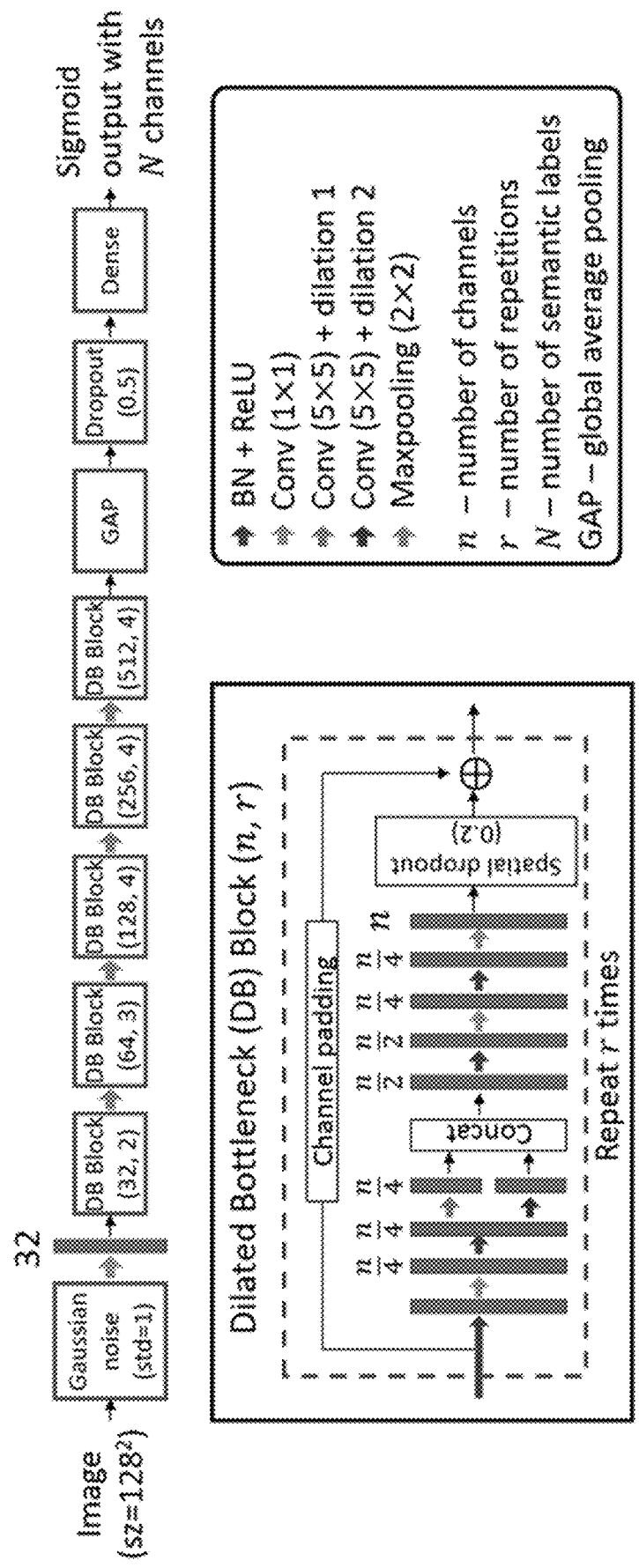
FIG. 3 shows a network architecture used in an example implementation of the system of FIG. 1 and the method of FIG. 2.

The custom architecture comprises the proposed Dilated Bottleneck (DB) blocks shown in FIG. 3. In each block, the efficient bottleneck architecture of ResNet was used so that deeper network can be trained. Dilated convolutions with dilation rates of 1 and 2 were also used to aggregate multi-scale context. Identity mappings and pre-activations were used for better information propagation, and spatial dropouts with dropout probability of 0.2 were used to alleviate overfitting. Therefore, each block allows efficient learning of multi-scale information. To further alleviate overfitting, a Gaussian noise layer, global average pooling, and dropout with probability of 0.5 were used with the cascaded DB blocks to form the network architecture. Images were resized to 128×128 with this architecture.

DenseNet neural network architecture was also used for the same problem to show the improvements from modifiers can be repeated on other networks. DenseNet neural network architecture utilizes skip connections to feed information to latter layers. DenseNet neural network architecture was used with 201 layers, and 18,319,554 trainable parameters.

E. Training Strategy

Image augmentation with rigid transformations was used to avoid overfitting. Because most of an image should be included, the augmentation was limited to rotation (10 degrees), shifting (10%), and scaling ([0.95, 1.05]). The probability of an image to be transformed was 80%. The optimizer Adam was used with a learning rate of $10^{-4}$, a batch size of 64, and 20 epochs.

An IBM POWER9 Accelerated Computer Server (AC922) was used that was designed to accommodate the data-intensive characteristics of modern analytics and AI workloads by fully exploiting its GPU capabilities, eliminating I/O bottlenecks and sharing memory across GPUs and CPUs. The machine was equipped with four V100 NVidia GPUs in its air-cooled configuration.

As a proof of concept, six semantic labels of three negated pairs ("consolidation", "no consolidation"), ("pneumothorax", "no pneumothorax"), and ("pulmonary edema", "no pulmonary edema") were used, resulting in 204 k frontal chest X-ray images. The choice of these pairs was intentional because these pairs have a high frequency in the MIMIC dataset and thus made the experiments statistically safe. The breakdown of samples is listed in Table 2.

training phase, at the time of testing, tests were only on samples that were not ambiguously labeled, so that the performance changes without ambiguity could be measured.

II. Results

One observation is that a large number of cases in MIMIC III radiology reports contained ambiguous disease findings (e.g. 50% ambiguous consolidation cases, 23% ambiguous pneumothorax cases, 66% ambiguous pulmonary edema cases). This shows the importance of modeling the ambiguity of labels during training.

A. Dilated Block Network

The baseline performance of Dilated block net on the six labels, along with the performance at best weight combination in the proposed method are reported in Table 3.

TABLE 3

Baseline and improved performance, in terms of area under ROC curve, of the two architectures.

|  | Consolidation | No Consolidation | Pneumothorax | No Pneumothorax | Pulmonary Edema | No Pulmonary Edema |
|---|---|---|---|---|---|---|
| Dilated Block, | 0.83 | 0.82 | 0.81 | 0.69 | 0.87 | 0.80 |
| baseline Dilated Block, $\mu = 0.8$ | 0.82 | 0.83 | 0.81 | 0.80 | 0.87 | 0.87 |
| DenseNet-201, | 0.83 | 0.83 | 0.81 | 0.72 | 0.87 | 0.81 |
| baseline DenseNet 201 $\mu = 0.9$ | 0.83 | 0.84 | 0.82 | 0.80 | 0.88 | 0.87 |

In Table 3, there was marked improvement of the No Pulmonary and No Pneumothorax labels when the ambiguity modeling is performed with appropriate weight values.

Figure 4:
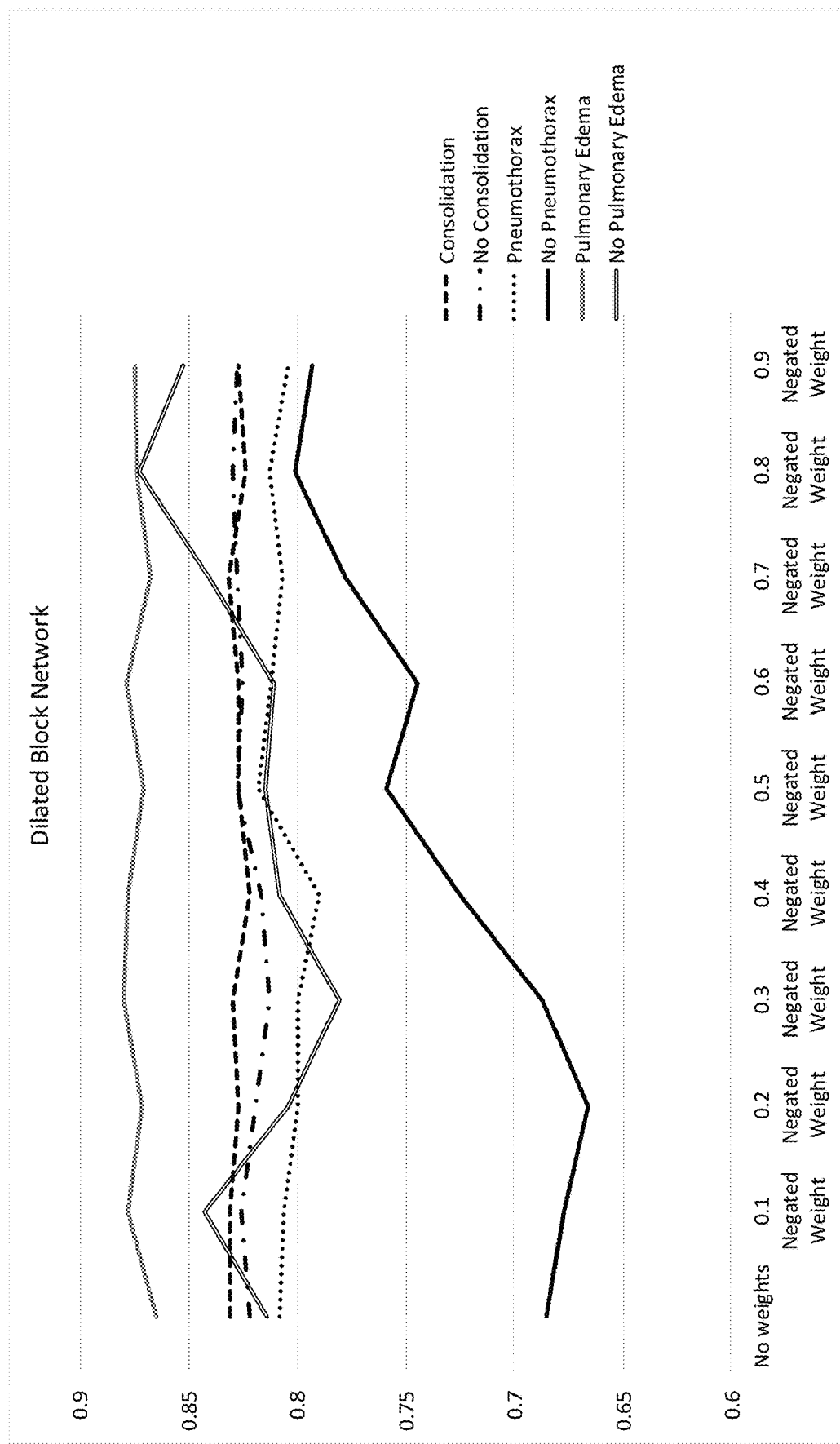
FIG. 4 is a chart from the example implementation showing an area under a receiver operating characteristic (ROC) curve for dilated block network architecture for varying values of weight modifier for negated findings.

FIG. 4 depicts the ROC per label for all combinations of weights for $\mu=0.1$ to $\mu=0.9$. The optimal weight was $\mu=0.8$, chosen based on average area under ROC curve for all six findings. The improvement was primarily on the negated labels. The area under ROC curve for no pneumothorax increases from 0.69 to 0.80, and from 0.80 to 0.87 for no pulmonary edema. The performance change for no consolidation was smaller.

B. DenseNet Results

Figure 5:
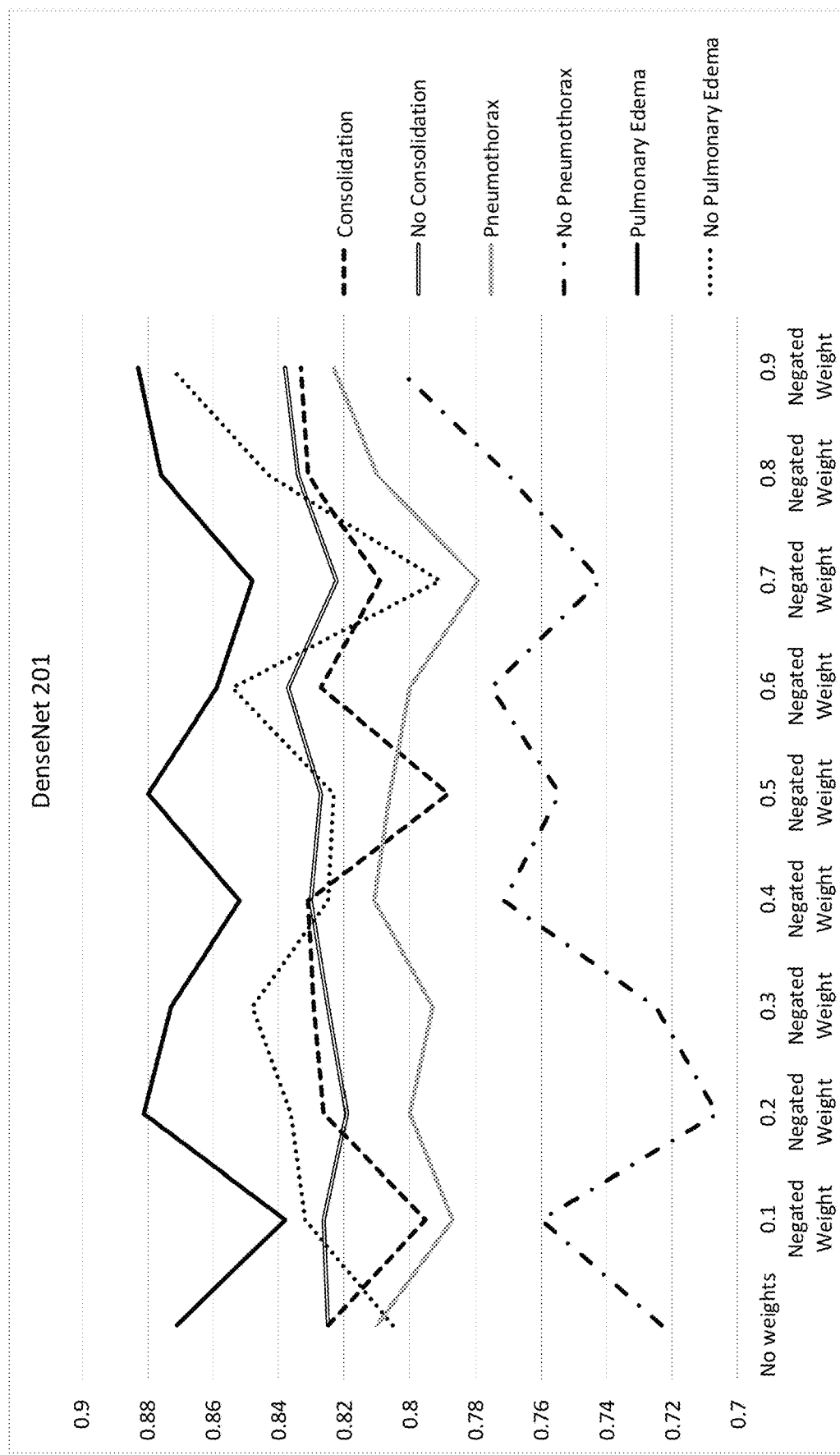
FIG. 5 is a chart from the example implementation showing an area under a ROC curve for DenseNet-201 architecture for varying values of weight modifier for negated findings.

DenseNet results are in FIG. 5 and the second half of Table 3. The optimal weight was $\mu=0.9$. Again the improvement is primarily on the negated with the area under ROC curve for no pneumothorax increasing from 0.72 to 0.80, and from 0.81 to 0.87 for no pulmonary edema. The performance stays similar to baseline for positive findings.

TABLE 2

The break-down of images across labels.

|  | Consolidation | No Consolidation | Pneumothorax | No Pneumothorax | Pulmonary Edema | No Pulmonary Edema |
|---|---|---|---|---|---|---|
| Training | 12,088 | 57,920 | 2,443 | 107,750 | 15,517 | 32,967 |
| Validation | 1,677 | 8,278 | 397 | 15,474 | 2,226 | 4,576 |
| Testing | 3,413 | 16,461 | 709 | 30,711 | 4,449 | 9,317 |

Figure 7:
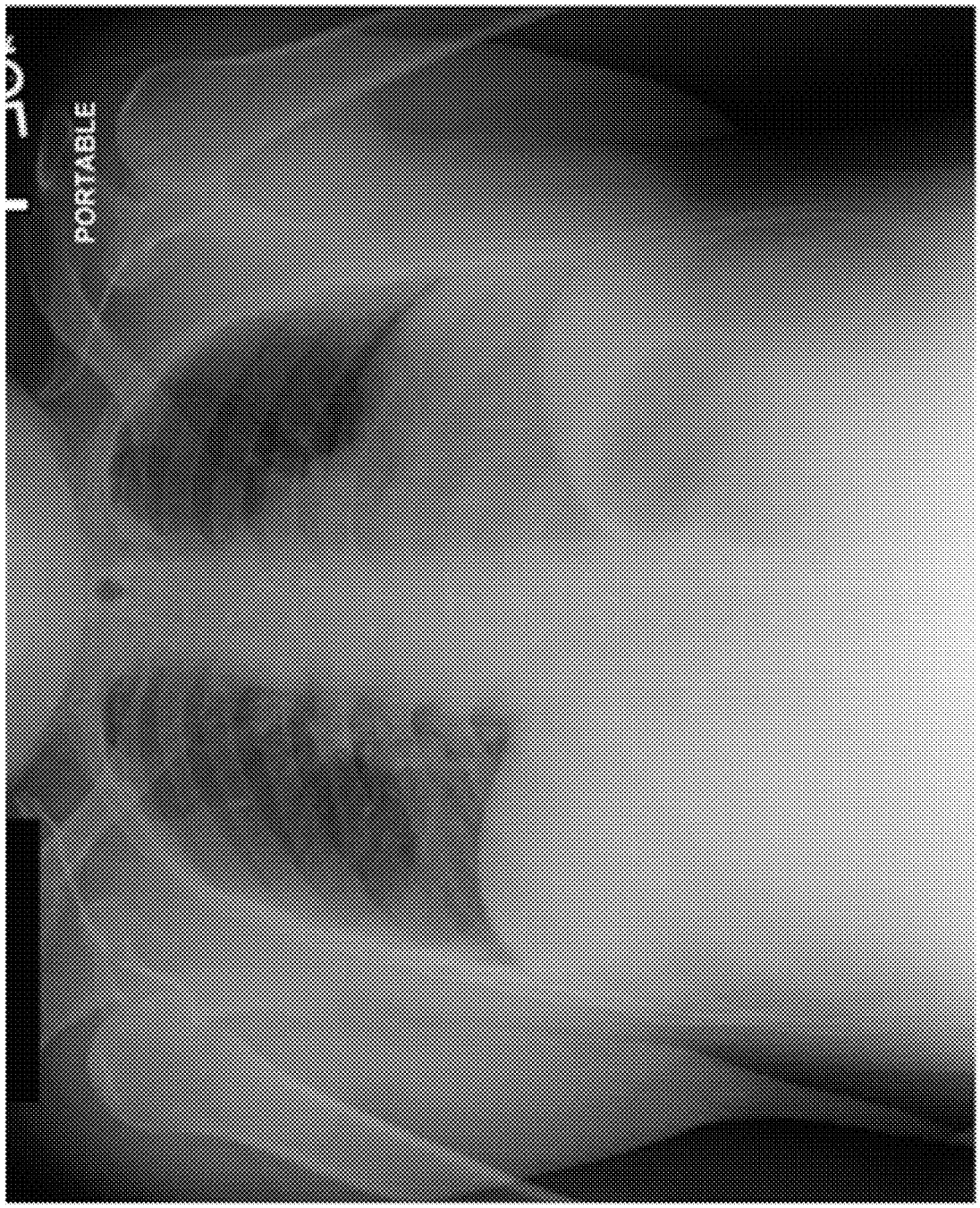
FIG. 7 is a second example from the example implementation of misclassification on baseline DenseNet neural network architecture, wherein the original report written by the radiologist read: "There is no pneumothorax pulmonary edema or pleural effusion. Hilar contours are within normal limits. Patient is status median sternotomy. There is no consolidation concerning for pneumonia."
Figure 8:
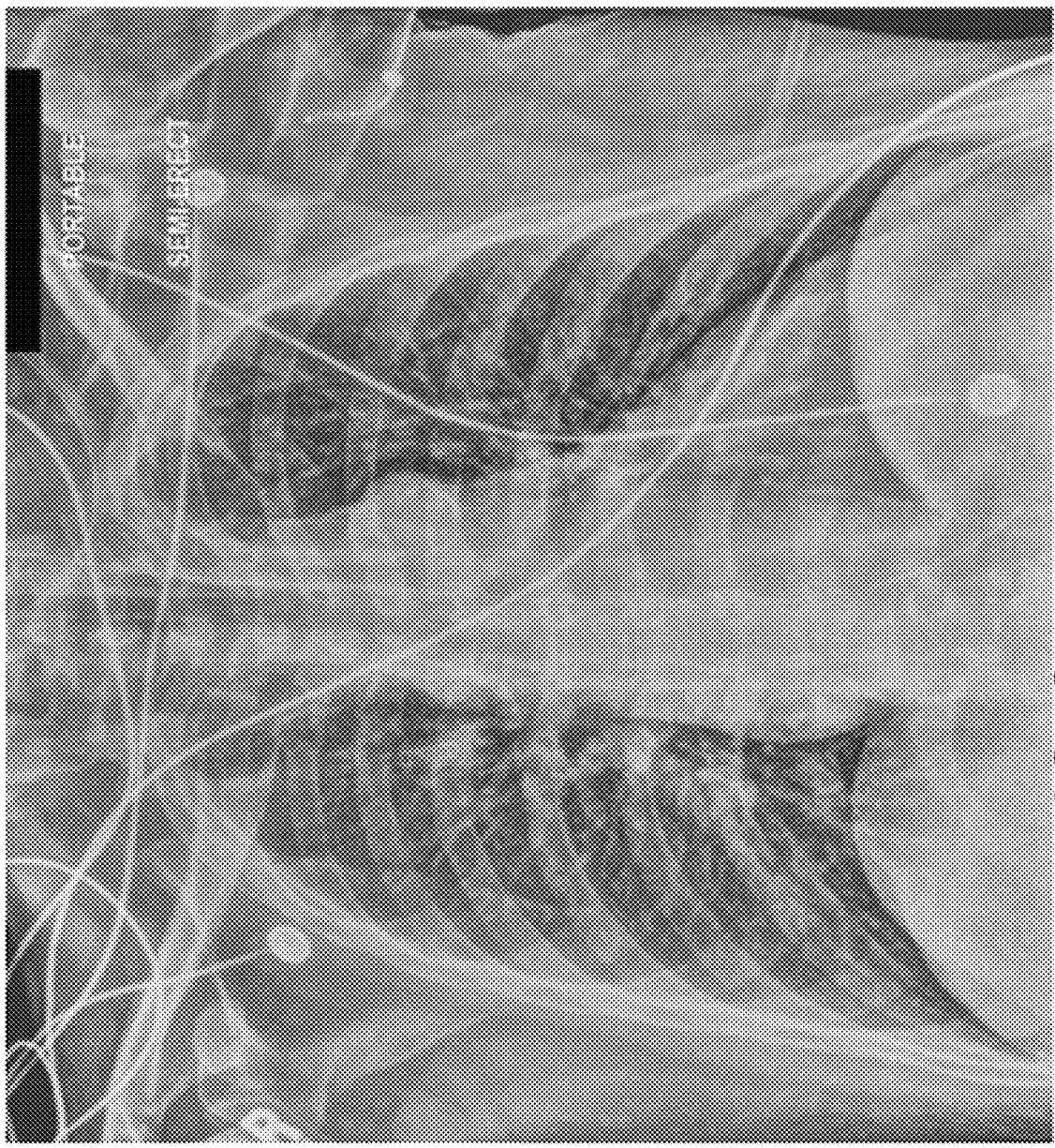
FIG. 8 is a third example from the example implementation of misclassification on baseline DenseNet neural network architecture, wherein the original report written by the radiologist read: "No evidence of pneumonia. No pulmonary edema large pleural effusions or pneumothorax. The mediastinum and heart are within normal limits."

The dataset was divided into 70% for training, 10% for validation, and 20% for testing, and the testing results were reported. Different values of $\mu$ in (3) were investigated. A value of 0.9 means a semantic label was trusted more than its negation, and a value of 0.1 means the opposite. Note that while all possible sample combinations were included in the C. Examples of Corrections Since the test set consisted of only non-ambiguous labels, the performance improvement translated to objectively more accurate findings. Nevertheless, for illustration purposes, FIGS. 6-8 show three examples within the test set of cases where the use of the proposed weight modifiers at the time of training changed the prediction from false positive to true negative.

Figure 6:
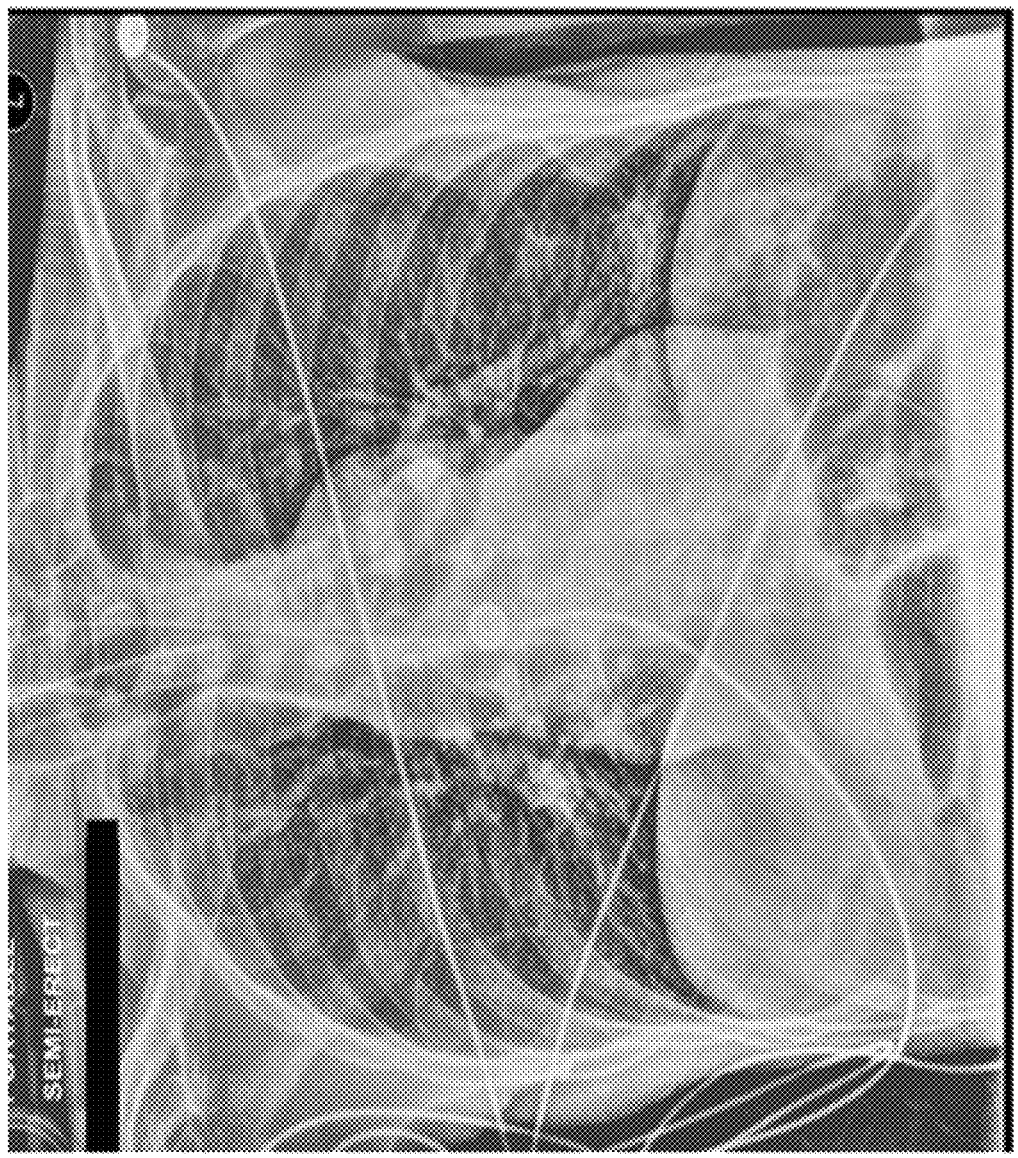
FIG. 6 is a first example from the example implementation of misclassification on baseline DenseNet neural network architecture, wherein the original report written by the radiologist read: "The lungs are otherwise free of focal consolidations pleural effusions or pneumothorax. No pulmonary edema. Minimal atelectasis at the left lung base. Cardiomediastinal silhouette is within normal limits."

For FIG. 6, the original report written by the radiologist read: "The lungs are otherwise free of focal consolidations pleural effusions or pneumothorax. No pulmonary edema. Minimal atelectasis at the left lung base. Cardiomediastinal silhouette is within normal limits." For FIG. 7, the original report written by the radiologist read: "There is no pneumothorax pulmonary edema or pleural effusion. Hilar contours are within normal limits. Patient is status median sternotomy. There is no consolidation concerning for pneumonia." For FIG. 8, the original report written by the radiologist read: "No evidence of pneumonia. No pulmonary edema large pleural effusions or pneumothorax. The mediastinum and heart are within normal limits."

III. Example Conclusions

The foregoing example presented a methodology to deal with ambiguity of disease findings in radiology reports. The approach to model this ambiguity was to add a class weight modifier and evaluate a range of weights from 0.1 to 0.9 for impact on classification accuracy in non-ambiguous test cases. For this example, an optimal balance of probabilities was that 80-90% of the ambiguous cases are negated disease findings. This was verified by two independent state-of-the-art neural networks evaluated on many images. Also observed was a large improvement in negated disease findings classification on a large dataset, while maintaining similar levels of accuracy in positive disease findings.

Accordingly, embodiments described herein improve the rule-out accuracy of deep disease detection using class weight modifiers. As noted above, image data sets used for training often include ambiguities regarding particular findings, such as when a radiologist does not positively nor negatively indicate the detect of a particular disease, and these ambiguities can affect performance of algorithms used to automatically detect the disease. To solve these and other problems, embodiments described herein apply labels to ambiguous findings, such as by applying reasonable class modifiers to a loss function for ambiguous ("no mention") cases, during training to improve the performance of resulting classification models.

Various features and advantages of the embodiments described herein are set forth in the following claims.

What is claimed is:

1. A system for training an artificial intelligence engine, the system comprising:
an electronic processor; and
memory storing instructions that, when executed by the electronic processor, cause the system to:
obtain a set of reports corresponding to a set of medical images;
for each report in the set of reports, determine whether the report includes a label for a finding of interest and, in response to determining that a label for the finding of interest was not mentioned in the report, identify the report as an ambiguous report;
generate a predicted label for the finding of interest for each report identified as an ambiguous report in the set of reports; and
train the artificial intelligence engine using a training set including each ambiguous report with the predicted label and each non-ambiguous report in the set of reports, thereby generating a classification model for the label for the finding of interest.

2. The system according to claim 1, wherein the memory further includes instructions that, when executes by the electronic processor, cause the system to:
apply natural language processing to the set of reports.

3. The system according to claim 2, wherein applying natural language processing includes applying context recognition natural language processing to differentiate between negative labels and positive labels for the finding of interest.

4. The system according to claim 1, wherein generating the predicted label for each report identified as an ambiguous report using a normal distribution to assign each report identified as an ambiguous report a positive label or a negative label.

5. The system according to claim 4, wherein the normal distribution is based on clinical data.

6. The system according to claim 4, wherein at least 80% of the predicted labels are negative labels.

7. The system according to claim 4, wherein at least 90% of the predicted labels are negative labels.

8. The system according to claim 1, wherein the set of medical images are chest x-ray images.

9. The system according to claim 1, wherein the memory further includes instructions that, when executed by the electronic processor, cause the system to:
apply the classification model in a subsequent analysis by the artificial intelligence engine.

10. A method for training an artificial intelligence engine hosted on a server, the method comprising:
obtaining a set of reports corresponding to a set of medical images;
applying natural language processing to the set of reports;
for each report in the set of reports, determining whether the report includes a label for a finding of interest and, in response to determining that a label for the finding of interest was not mentioned in the report, identifying the report as an ambiguous report;
generating, using an electronic processor, a predicted label for the finding of interest for each report identified as an ambiguous report in the set of reports; and
training the artificial intelligence engine using a training set including each ambiguous report with the predicted label and each non-ambiguous report in the set of reports, thereby generating a classification model for the finding of interest.

11. The method according to claim 10, wherein applying natural language processing includes applying context recognition natural language processing to differentiate between negative labels and positive labels for the finding of interest.

12. The method according to claim 11, wherein generating the predicted label for each report identified as an ambiguous report includes using a normal distribution to assign each report identified as an ambiguous report a positive label or a negative label.

13. The method according to claim 12, wherein the normal distribution is based on clinical data.

14. The method according to claim 13, wherein 80%-90% of the predicted labels are negative labels.

15. The method according to claim 14, wherein the set of medical images are chest x-ray images.

16. The method according to claim 15, further comprising applying the classification model in a subsequent analysis by the artificial intelligence engine.

17. Non-transitory computer-readable medium storing instructions that, when executed by an electronic processor, perform a set of functions, the set of functions comprising:

obtaining a set of reports corresponding to a set of medical images;

applying natural language processing to the set of reports;

for each report in the set of reports, determining whether the report includes a label for a finding of interest and, in response to determining that a label for the finding was not mentioned in the report, identifying the report as an ambiguous report;

generating a predicted label for the finding of interest for each report identified as an ambiguous report in the set of reports; and training the artificial intelligence engine using a training set including each ambiguous report with the predicted label and each non-ambiguous report in the set of reports, thereby generating a classification model for the finding of interest.

18. The non-transitory computer-readable medium according to claim 17, wherein applying natural language processing includes applying context recognition natural language processing to differentiate between negative labels and positive labels for the finding of interest; and wherein generating the predicted label for each report identified as an ambiguous report includes using a normal distribution to assign each report identified as an ambiguous report a positive label or a negative label.

19. The non-transitory computer-readable medium according to claim 18, wherein the normal distribution is based on clinical data; and wherein 80%-90% of the predicted labels are negative labels.

20. The non-transitory computer-readable medium according to claim 19, wherein the set of functions further comprises:

applying the classification model in a subsequent analysis by the artificial intelligence engine, wherein the set of medical images are chest x-ray images.

* * * * *